United States Patent
Hakim et al.

(10) Patent No.: US 10,898,699 B2
(45) Date of Patent: Jan. 26, 2021

(54) VAGINAL STENTS, VAGINAL DILATORS, AND METHODS OF FABRICATING THE SAME

(71) Applicant: Baylor College of Medicine, Houston, TX (US)

(72) Inventors: Julie Hakim, Houston, TX (US); Jennifer Elizabeth Dietrich, Houston, TX (US); Peter Alexander Smith, Houston, TX (US); Cara Buskmiller, Richmond Heights, MO (US)

(73) Assignee: Baylor College of Medicine, Houston, TX (US)

( * ) Notice: Subject to any disclaimer, the term of this patent is extended or adjusted under 35 U.S.C. 154(b) by 295 days.

(21) Appl. No.: 15/565,330

(22) PCT Filed: Apr. 4, 2016

(86) PCT No.: PCT/US2016/025826
§ 371 (c)(1),
(2) Date: Oct. 9, 2017

(87) PCT Pub. No.: WO2016/167996
PCT Pub. Date: Oct. 20, 2016

(65) Prior Publication Data
US 2018/0071502 A1 Mar. 15, 2018

Related U.S. Application Data

(60) Provisional application No. 62/147,285, filed on Apr. 14, 2015, provisional application No. 62/300,295, filed on Feb. 26, 2016.

(51) Int. Cl.
*A61M 29/02* (2006.01)
*A61B 17/52* (2006.01)
(Continued)

(52) U.S. Cl.
CPC ............ *A61M 29/02* (2013.01); *A61B 17/42* (2013.01); *A61B 17/52* (2013.01); *A61B 5/1076* (2013.01);
(Continued)

(58) Field of Classification Search
CPC .................. A61B 1/303; A61B 17/42; A61B 17/4216–4225; A61B 17/4241;
(Continued)

(56) References Cited

U.S. PATENT DOCUMENTS 3,812,841 A * 5/1974 Isaacson ............... A61F 2/0022
600/29
5,514,091 A * 5/1996 Yoon ................... A61B 17/3439
604/103.11
(Continued)

FOREIGN PATENT DOCUMENTS

| CN | 1913833 A | 2/2007 |
|---|---|---|
| DE | 3800744 C1 | 5/1989 |

(Continued)

OTHER PUBLICATIONS

Extended European Search Report, European Patent Application No. 16780458.2, dated Nov. 12, 2018.
(Continued)

*Primary Examiner* — Katrina M Stransky
*Assistant Examiner* — Brigid K Byrd
(74) *Attorney, Agent, or Firm* — Saul Ewing Arnstein & Lehr LLP; Kathryn Doyle; Brian R. Landry

(57) ABSTRACT

One aspect of the invention provides a vaginal stent system including: an inflatable vaginal stent and a removable handle. The inflatable vaginal stent include includes: an elastomeric exterior wall and a first fitting located at a base of the inflatable vaginal stent. The removable handle is adapted and configured for insertion, inflation, and removal
(Continued)

of the inflatable vaginal stent from a subject's vagina. The removable handle includes a second fitting complementary to the first fitting and adapted and configure to form substantially fluid tight coupling when the handle is coupled to the inflatable vaginal stent. Another aspect of the invention provides a method of fabricating a customized vaginal stent or dilator. The method includes: generating a 3D model of a vaginal stent or dilator; and controlling a 3D printer to fabricate a vaginal stent or dilator according to the 3D model.

8 Claims, 11 Drawing Sheets

(51) Int. Cl.
| | |
|---|---|
| *A61B 17/42* | (2006.01) |
| *A61B 17/00* | (2006.01) |
| *A61B 5/00* | (2006.01) |
| *A61B 5/107* | (2006.01) |
| *A61M 25/01* | (2006.01) |
| *A61M 25/10* | (2013.01) |
| *A61B 34/10* | (2016.01) |

(52) U.S. Cl.
CPC ............ *A61B 5/4337* (2013.01); *A61B 34/10* (2016.02); *A61B 2017/0046* (2013.01); *A61B 2017/00526* (2013.01); *A61B 2017/00557* (2013.01); *A61B 2017/00876* (2013.01); *A61B 2034/108* (2016.02); *A61M 25/0127* (2013.01); *A61M 2025/1054* (2013.01); *A61M 2205/0216* (2013.01); *A61M 2207/00* (2013.01); *A61M 2210/1475* (2013.01)

(58) Field of Classification Search
CPC .. A61F 5/003; A61M 29/00–2029/025; A61M 25/10186
See application file for complete search history.

(56) References Cited

U.S. PATENT DOCUMENTS

| | | | |
|---|---|---|---|
| 5,716,329 A | | 2/1998 | Dieter |
| 6,102,929 A | * | 8/2000 | Conway ............ A61M 25/0075 606/192 |
| 6,224,580 B1 | | 5/2001 | Christensen |
| 6,293,923 B1 | * | 9/2001 | Yachia ................. A61F 2/0027 600/29 |
| 2004/0030352 A1 | | 2/2004 | McGloughlin et al. |
| 2005/0021069 A1 | | 1/2005 | Feuer et al. |
| 2007/0043388 A1 | | 2/2007 | Greenwood |
| 2008/0200872 A1 | * | 8/2008 | Isham ............... A61M 25/1002 604/96.01 |
| 2010/0082057 A1 | | 4/2010 | Borkon |
| 2010/0094082 A1 | * | 4/2010 | Iinuma ............... A61B 1/00165 600/105 |
| 2010/0136088 A1 | | 6/2010 | Sulger |
| 2013/0267868 A1 | | 10/2013 | Connors et al. |
| 2014/0200605 A1 | | 7/2014 | Jones et al. |
| 2015/0170416 A1 | | 6/2015 | McGregor et al. |

FOREIGN PATENT DOCUMENTS

| | | |
|---|---|---|
| WO | 2011116108 A1 | 9/2011 |
| WO | WO 2015/013716 A1 | 1/2015 |

OTHER PUBLICATIONS

Accenture, "The MedTech Disconnect: Realigning Innovation to Succeed", Accenture Life Sciences, 2014.
Hakim, J., et al., "Innovative Use of 3D Printers in Gynecology", J Pediatr Adolesc Gynecol 28 (2015) e41ee78.
MatterHackers, 3D Printing Materials, Filament Comparison Guide, https://www.matterhackers.com/3d-printer-filament-compare, downloaded Apr. 10, 2015.
Owen Mumford, Amielle Comfort Vaginal dilators, downloaded Apr. 9, 2015.
Porges, Vaginal Stent, http://www.porges.com/en-uk/female-pelvic-health/vaginal-stents/, downloaded Apr. 9, 2015.
Stratasys, Objet30 Pro, downloaded Apr. 10, 2015.
Stratasys, Safety Data Sheet: OBJET RGD525, Feb. 2013.
Vaginismus.com, Vaginal Dilators, 2013.
International Search Report and Written Opinion, PCT Application No. PCT/US2016/025826, dated Jul. 22, 2016.
First Office Action, Chinese Patent Application No. 2016800220210, dated Dec. 3, 2019.
Second Office Action, China Patent Application No. 201680022021.0, dated Jun. 8, 2020.

* cited by examiner

VAGINAL STENTS, VAGINAL DILATORS, AND METHODS OF FABRICATING THE SAME

CROSS-REFERENCES TO RELATED APPLICATIONS

This application is a national phase application of International Application No. PCT/US2016/025826, filed Apr. 4, 2016, which claims priority to U.S. Provisional Patent Application Ser. No. 62/147,285, filed Apr. 14, 2015, and U.S. Provisional Patent Application Ser. No. 62/300,295, filed Feb. 26, 2016. The entire contents of each of these applications is hereby incorporated by reference herein.

BACKGROUND OF THE INVENTION

Vaginal dilators and stents are used after surgical neovagina creation in order to maintain the caliber of the newly created vagina and to avoid restenosis after surgery or radiation. Neovaginal creation is necessary in girls born with Mayer-Rokitansky-Küster-Hauser (MRKH) syndrome (1/4,500), vaginal agenesis (1/5,000-7,000), cloacal anomalies, Congenital Adrenal Hyperplasia or other congenital anomalies. Additional uses include any women with vaginal stenosis from pelvic radiation or gynecology-oncology related cancer surgeries.

Currently available stents and dilators exist only in adult vaginal sizes that cannot be used safely or comfortably in the pediatric population or oncologic patients who have undergone vaginal brachytherapy.

SUMMARY OF THE INVENTION

One aspect of the invention provides a vaginal stent system including: an inflatable vaginal stent and a removable handle. The inflatable vaginal stent include includes: an elastomeric exterior wall and a first fitting located at a base of the inflatable vaginal stent. The removable handle is adapted and configured for insertion, inflation, and removal of the inflatable vaginal stent from a subject's vagina. The removable handle includes a second fitting complementary to the first fitting and adapted and configure to form substantially fluid tight coupling when the handle is coupled to the inflatable vaginal stent.

This aspect of the invention can have a variety of embodiments. At least one of the inflatable vaginal stent and the removable handle can include one or more magnets. The inflatable vaginal stent can include a magnetically-actuatable valve adapted and configured to deflate the inflatable vaginal stent when the removable handle is placed in proximity to a base of the inflatable vaginal stent. The one or more magnets can have sufficient strength to remove the inflatable vaginal stent from a subject's vagina by placing the removable handle proximate to the subject's perineum.

Another aspect of the invention provides a vaginal dilator system including: a vaginal dilator and a removable handle. The vaginal dilator includes: an exterior wall and a hollow channel extending the length of the vaginal stent. The removable handle is adapted and configured for insertion and removal of the inflatable vaginal stent from a subject's vagina.

This aspect of the invention can have a variety of embodiments. At least one of the vaginal dilator and the removable handle can include one or more magnets. The one or more magnets can have sufficient strength to remove the inflatable vaginal stent from a subject's vagina by placing the removable handle proximate to the subject's perineum.

Another aspect of the invention provides a method of fabricating a customized vaginal stent or dilator. The method includes: generating a 3D model of a vaginal stent or dilator; and controlling a 3D printer to fabricate a vaginal stent or dilator according to the 3D model.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

DEFINITIONS

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

Methods of Fabricating Vaginal Stents or Dilators

Figure 1:
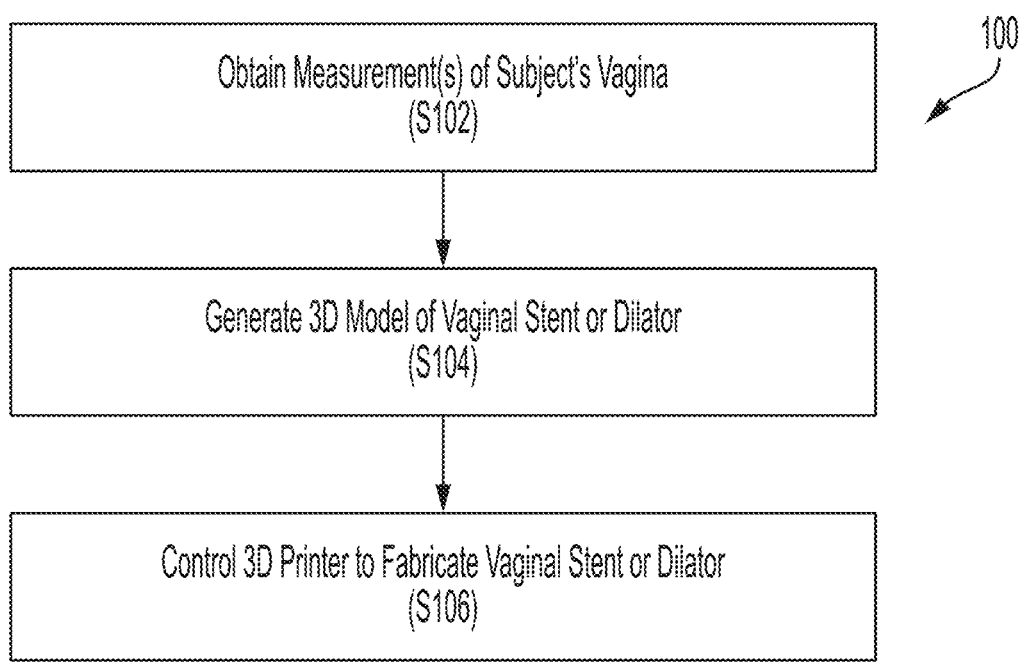
FIG. 1 depicts a method 100 of fabricating a vaginal stent or dilator according to an embodiment of the invention.

Referring now to FIG. 1, one aspect of the invention provides a method 100 of fabricating a vaginal stent or dilator.

Optionally in step S102, one or more measurements are obtained. The measurements can relate to the current dimensions of a subject's vagina or desired dimensions for various medical reasons. In some embodiments, the dimensions can be assessed visually by a healthcare provider. Additionally or alternatively, one or more imaging devices such as an inflatable cavity imager (e.g., as described in U.S. Patent Application Publication Nos. 2014/0272221, 2014/0276005, and 2014/0276105) or various ultrasound, magnetic resonance, computed tomography, and/or X-ray devices and techniques can be utilized.

In step S104, a 3D model of a vaginal stent or dilator is generated. The 3D model can be generated based on the one or more measurements obtained in step S102 or can be generated from one or more templates or patterns. The 3D model can be generated using computer-aided design (CAD) software and can be manipulated by a healthcare provider to have a desired shape and/or dimensions. In some embodiments, a stent has an uninflated dimension of about 7 cm in length by about 2 cm in width or about 6 cm in length by about 1 cm in width. In some embodiments, dilators can have lengths and diameters as small as about 0.5 cm.

In step S106, a 3D printer is controlled to fabricate a vaginal stent or dilator according to the 3D model generated in step S104. A variety of 3D printers are available from a variety of sources. One suitable 3D printer is the OBJET30 PRO™ 3D printer from Stratasys Ltd. of Eden Prairie, Minn., which deposits layers of liquid photopolymers. One exemplary photopolymer is OBJET RGD525 acrylic photopolymer also available from Stratasys Ltd. Other suitable photopolymers include acrylonitrile butadiene styrene (ABS), polypropylene, rubber, and the like. Suitable fused deposition modeling (FDM) thermoplastics include acrylonitrile butadiene styrene (ABS), acrylonitrile styrene acrylate (ASA), nylon, polycarbonate (PC), PC-ABS blends, polylactic acid (PLA), polyvinyl alcohol (PVA), thermoplastic elastomers (TPEs), high impact polystyrene (HIPS), and the like. Other suitable extrudable materials include silicone.

Fabrication of vaginal stents and dilators can provide customized devices to fit a particular subject's anatomy and medical needs without the delays associated with manufacturing and shipping. Additionally, customized fabrication can avoid the need to purchase multiple devices that may not fit the patient's anatomy or needs, and can reduce patient frustration, pain, and non-compliance.

In addition to 3D printing one or more components of a vaginal stent or dilator, 3D printing can also be utilized to produce negative molds of one or more components that can then be used to mold one or more components. For example, a negative of an uninflated exterior wall as described further herein can be printed using a 3D printer and then used to cast the exterior wall, e.g., with an elastomer such as polyurethane.

Vaginal Stents

Figure 2A:
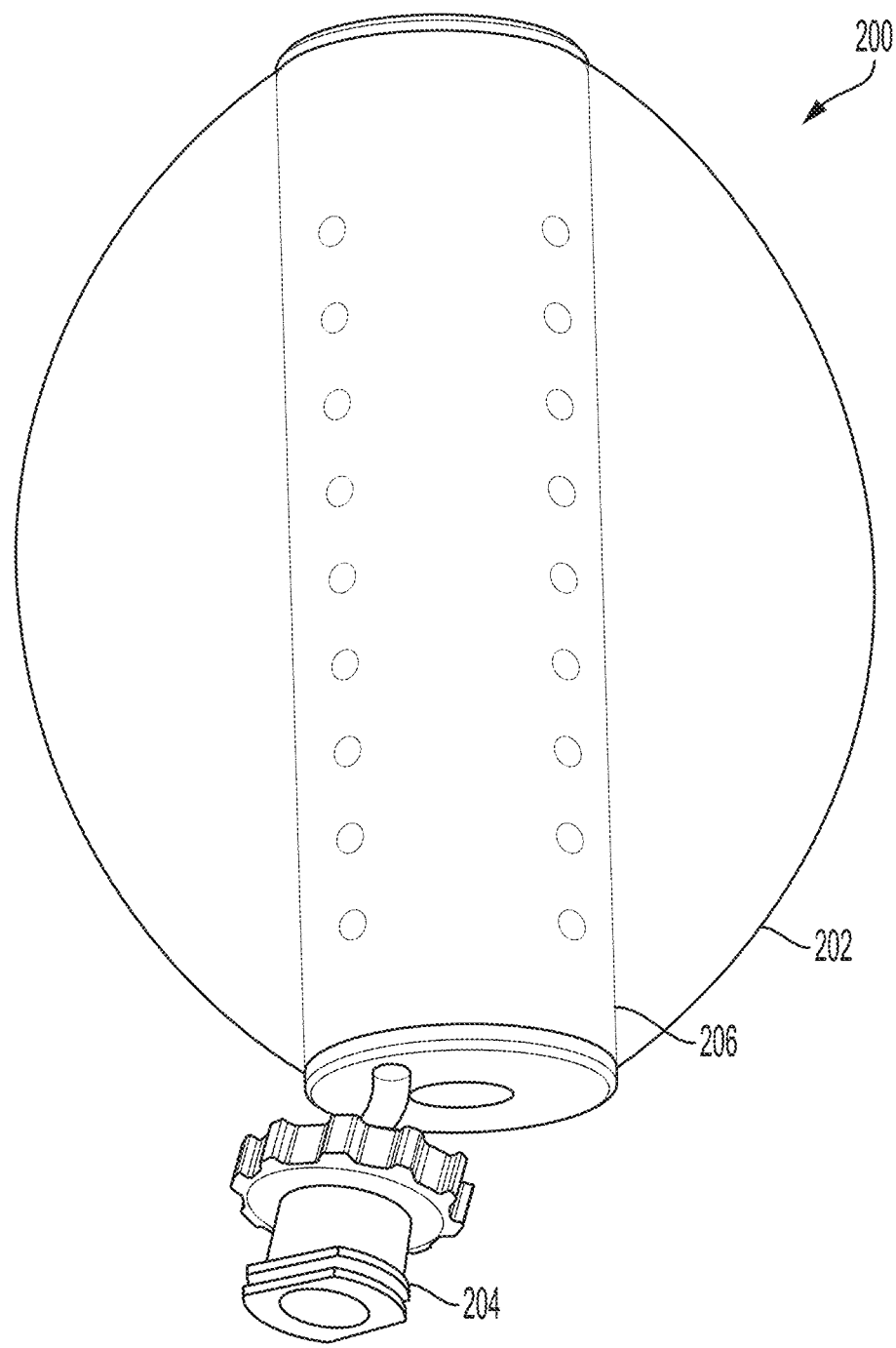
FIGS. 2A-2C depict perspective views of a vaginal stent according to an embodiment of the invention.

Referring now to FIG. 2A, another aspect of the invention provide a vaginal stent 200 that can be inserted into a subject's vagina and inflated to a desired size to achieve a medical goal. The vaginal stent 200 includes an elastomeric exterior wall 202 and a fitting 204 located at the base of the vaginal stent 200. When inflated, the stent 200 can be rigid enough to retain shape and vaginal wall support despite movement and valsalva. The stent 200 can be inserted intraoperatively, remain in situ, and be progressively inflated until removal at a later date when healing occurs.

The fitting 204 can be adapted and configured to receive a fluid (either gas or liquid) to inflate the elastomeric exterior wall 202 to a desired level and/or shape. In one embodiment, the fitting 204 is a Luer-lock-style fitting.

A central core 206 can maintain the length of and facilitate insertion of the stent 200 into the subject's vagina prior to inflation. The central core 206 can be pliable, while also having rebound and shape memory. The central core 206 can be fabricated from rubbers, plastics, or metals. In one embodiment, the central core 206 has a plurality of holes to facilitate flow of fluid into the region bound by the elastomeric exterior wall 202. In some embodiments, the inner core 206 is perforated or is a plastic mesh.

Figure 2B:
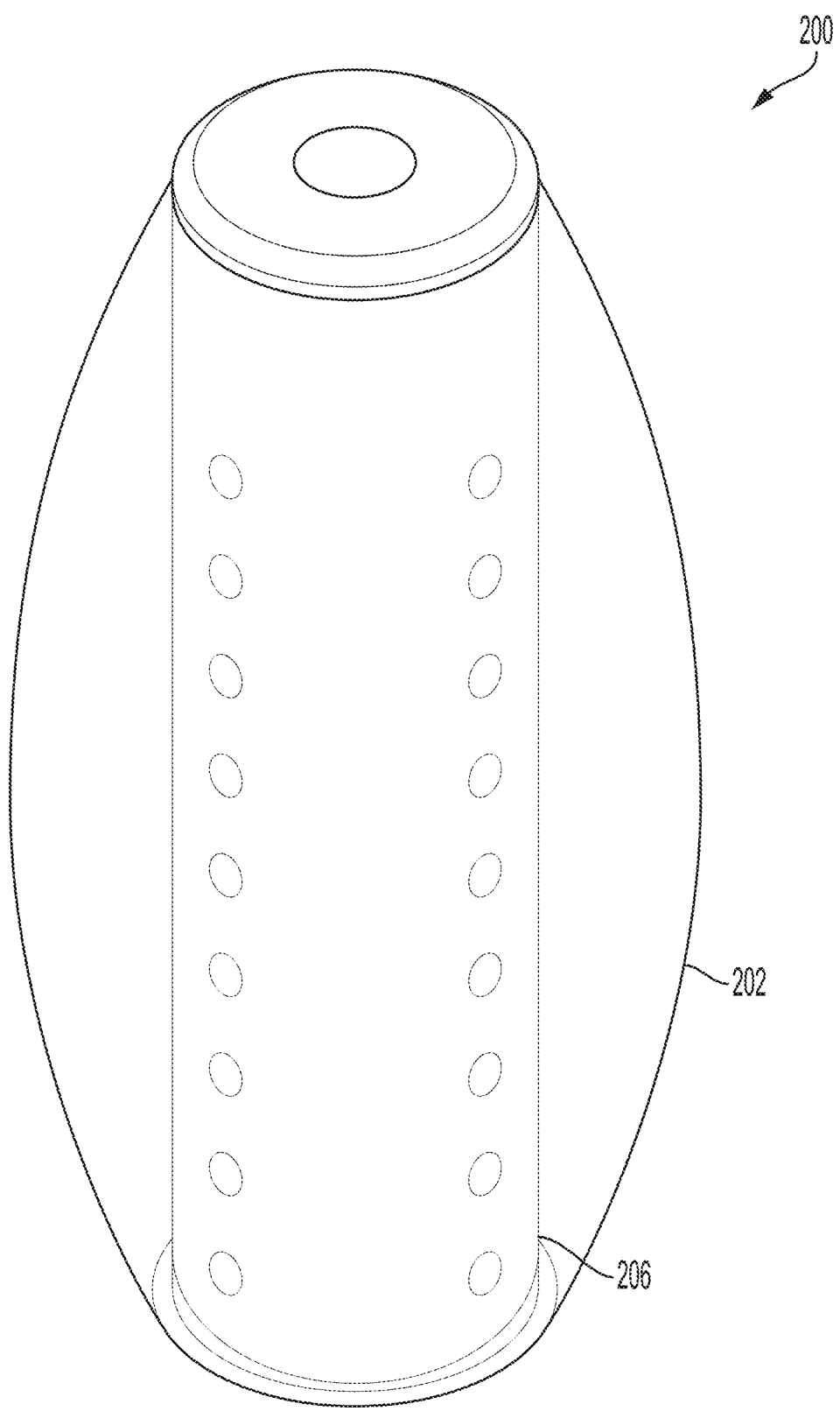
Figure 2C:
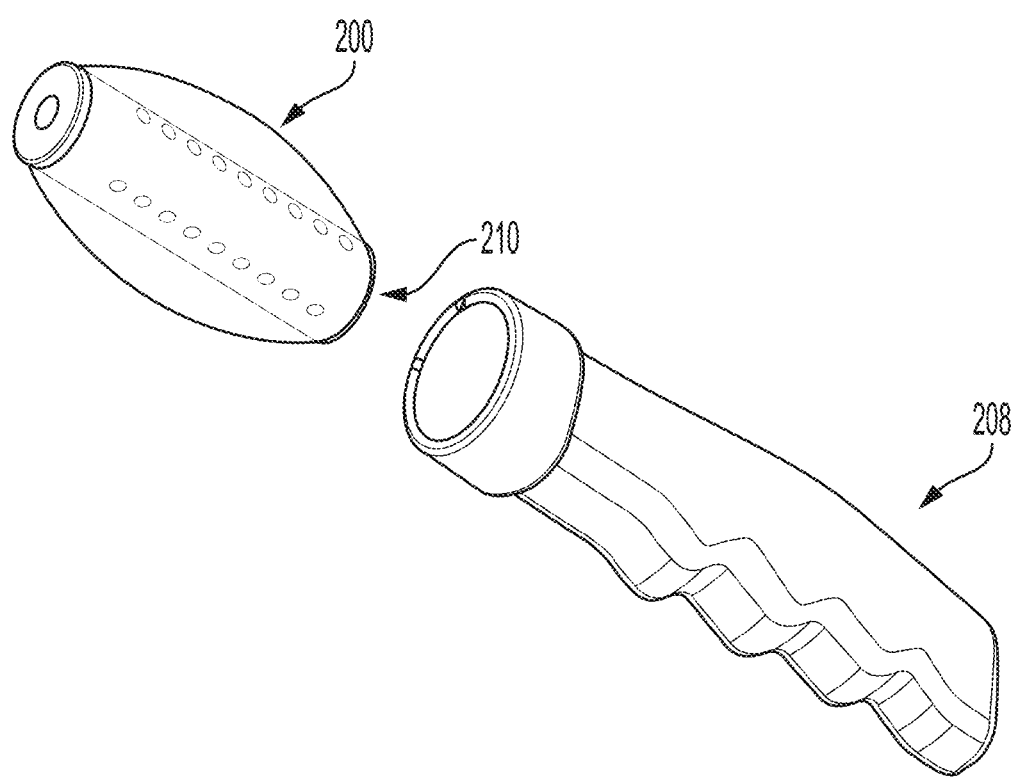

Insertion and removal of vaginal stents can be challenging and/or uncomfortable for many patients and particularly for children and adolescents. In order to address this discomfort, embodiments of the invention can utilize a removable handle 208 as depicted in FIG. 2B. One or more of the removable handle 208 and the vaginal stent 200 can include one or more magnets (e.g., 4 or 8) such as rare-earth magnets. In some embodiments, the magnets can have sufficient strength to pull the vaginal stent 200 from the subject's vagina when the subject holds the removable handle 208 adjacent or proximal to the subject's perineum. Without being bound by theory, it is believed that between about 0 pounds and about 26 pounds of force (e.g., between about 0 pounds and about 5 pounds, between about 5 pounds and about 10 pounds, between about 10 pounds and about 15 pounds, between about 15 pounds and about 20 pounds, between about 20 pounds and about 26 pounds, and the like) would be sufficient to remove a deflated vaginal stent from a typical subject's vagina and that sufficient force can be generated across the perineum using magnets.

In order to further minimize user discomfort, the removable handle can facilitate inflation and/or deflation of the magnetic stent. For example, the vaginal stent 200 can include one or more fittings located on a base that engages with the removable handle 208 and the removable handle 208 can include a complementary second fitting. For example, the fittings can be located centrally to a plurality of radially-arranged magnets and/or ferromagnetic materials so that fittings will be aligned by magnetic forces. Once the vaginal stent 200, the removable handle 208, and the fittings therein are engaged, fluid can flow from the removable handle into the vaginal stent 200 for inflation. One or more valves (e.g., one-way or check valves) can seal the vaginal stent 200 against fluid leakage. In one embodiment, one or more of the one or more valves 210 can be magnetically-actuated, preferably at a relatively low magnetic force so that the vaginal stent 200 will deflate as the removable handle 208 approaches the perineum and prior to the application of sufficient forces to move and extract the vaginal stent 200. In some embodiments, the removable handle 208 can include a pressure gauge to provide feedback to the subject regarding the degree of inflation of the coupled vaginal stent.

Figure 3A:
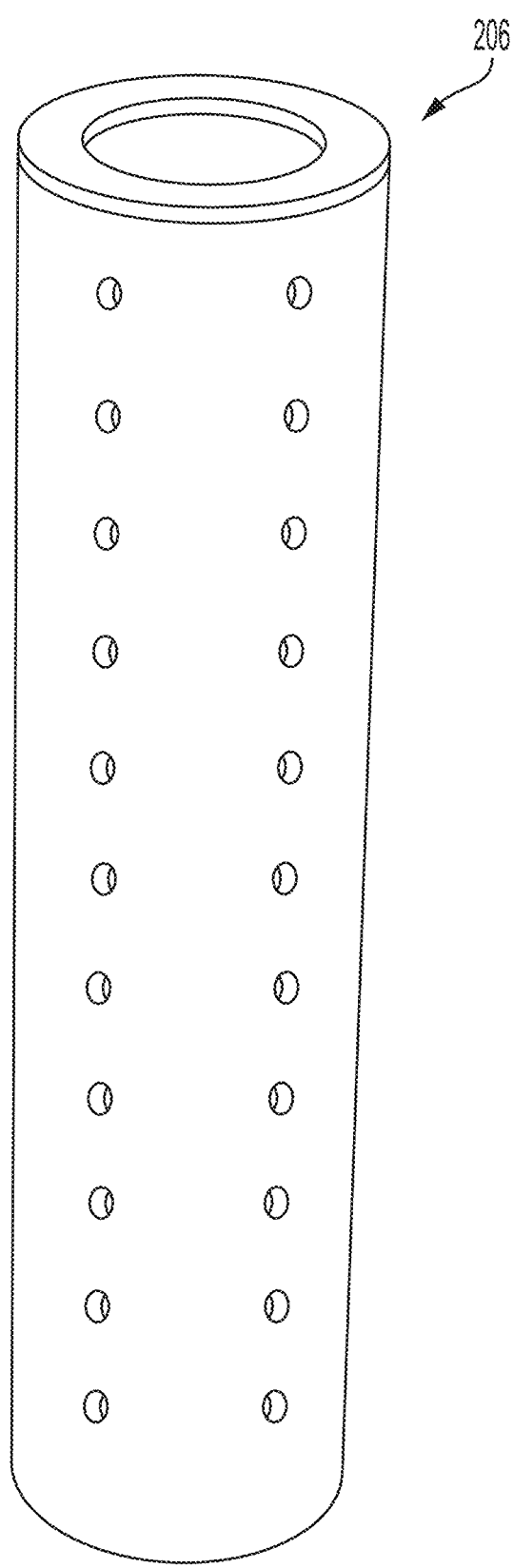
FIGS. 3A-3E depict various views of a core for a vaginal stent according to an embodiment of the invention.
Figure 3B:
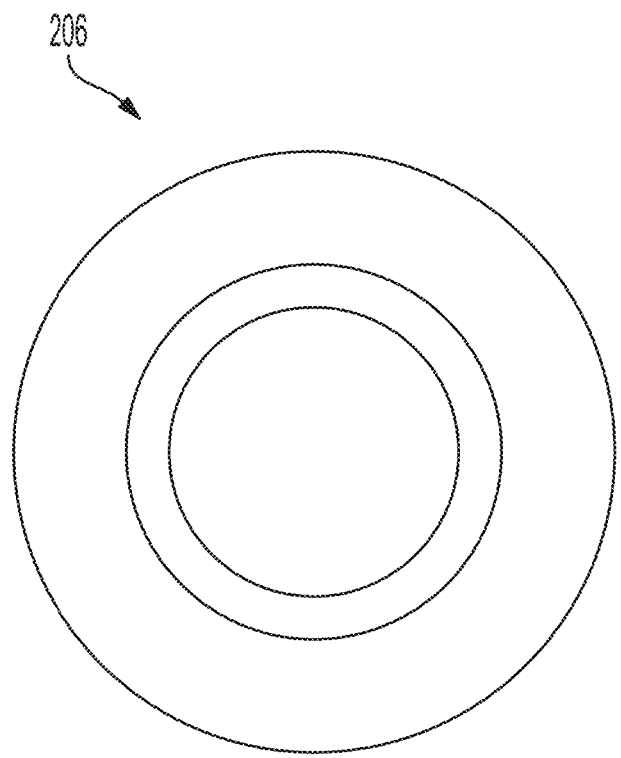
Figure 3C:
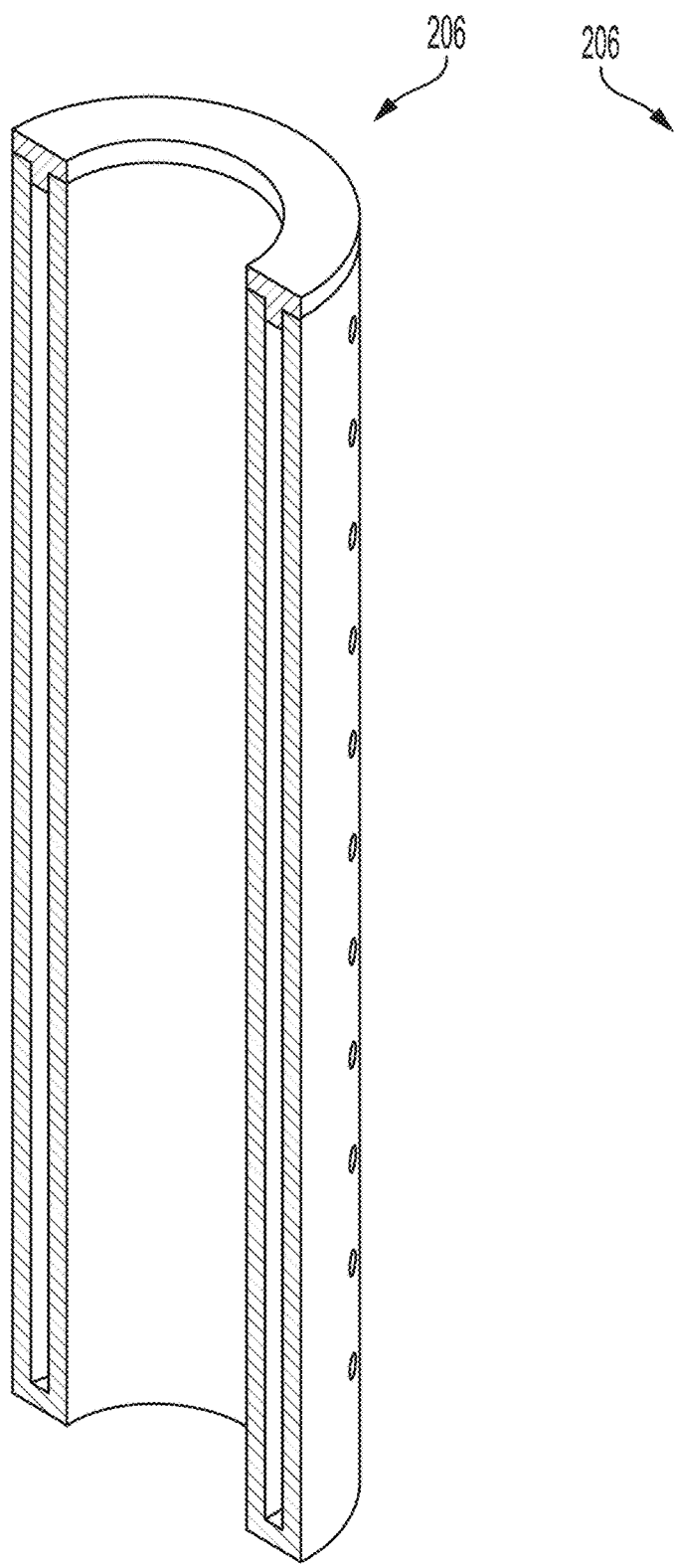
Figure 3D:
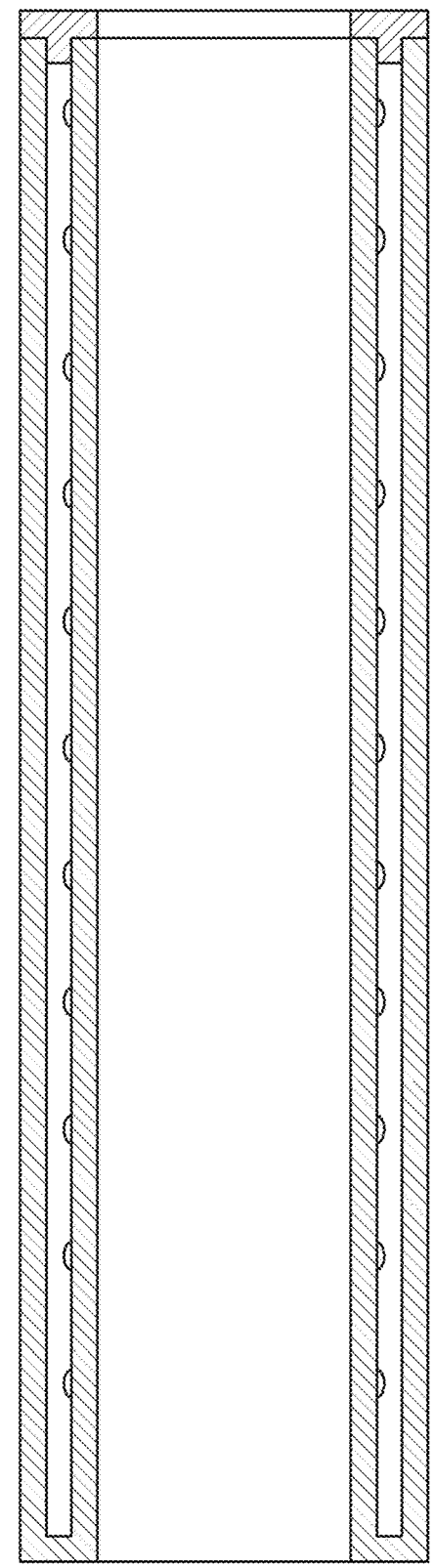
Figure 3E:
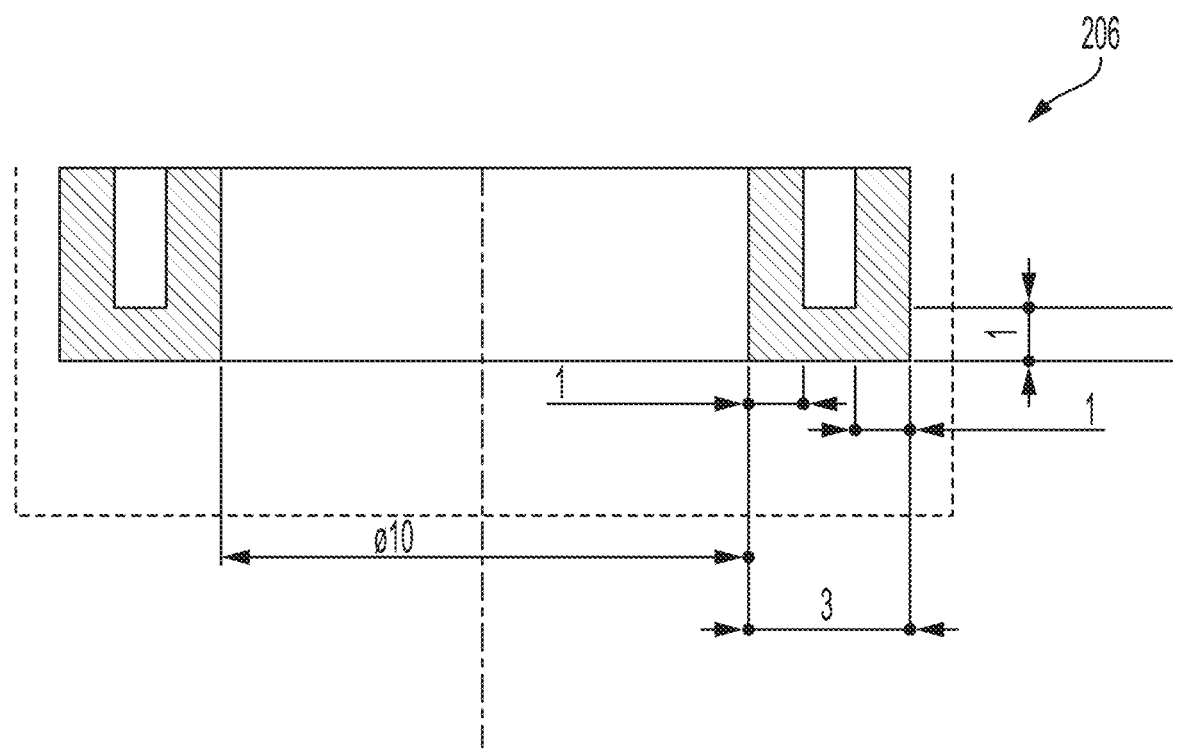

Referring now to FIGS. 3A and 3B, side and top views of the core 206 are provided showing the perforations in the outer wall and the hollow center and ends that allow for passage of vaginal secretions. FIGS. 3C-3E provide cross-sectional views of the core. FIG. 3E provides exemplary dimensions in millimeters.

Vaginal Dilator

Figure 4A:
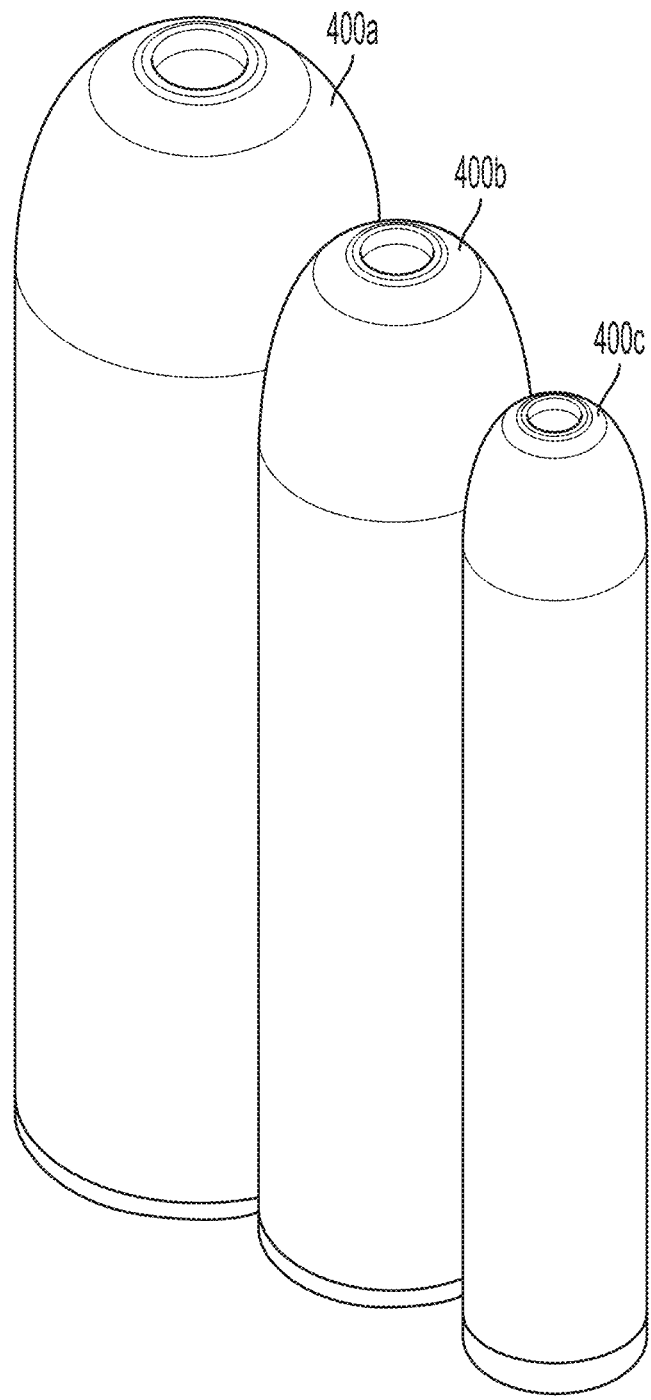
FIGS. 4A-4D depict vaginal dilators according to embodiments of the invention.

Referring now to FIG. 4A, another aspect of the invention provides vaginal dilators 400a, 400b, 400c that can be composed of a rigid, durable plastic material shaped as a tapered hollow capsule. Various sizes can be produced. For example, dilator 400a has a diameter of about 20 mm and a length of about 70 mm, dilator 400b has a diameter of about 15 mm and a length of about 65 mm, and dilator 400c has a diameter of about 10 mm and a length of about 60 mm. Any of the vaginal dilators disclosed herein may comprise a hollow channel for extrusion of fluid from the vagina as shown in FIG. 4A. In certain embodiments, the channel runs along the entire length of the vaginal dilator. The diameter of the channel is not restricted to any particular diameter, but should be sufficient for fluid to enter the channel and, in certain embodiments, to pass through the dilator.

Figure 4B:
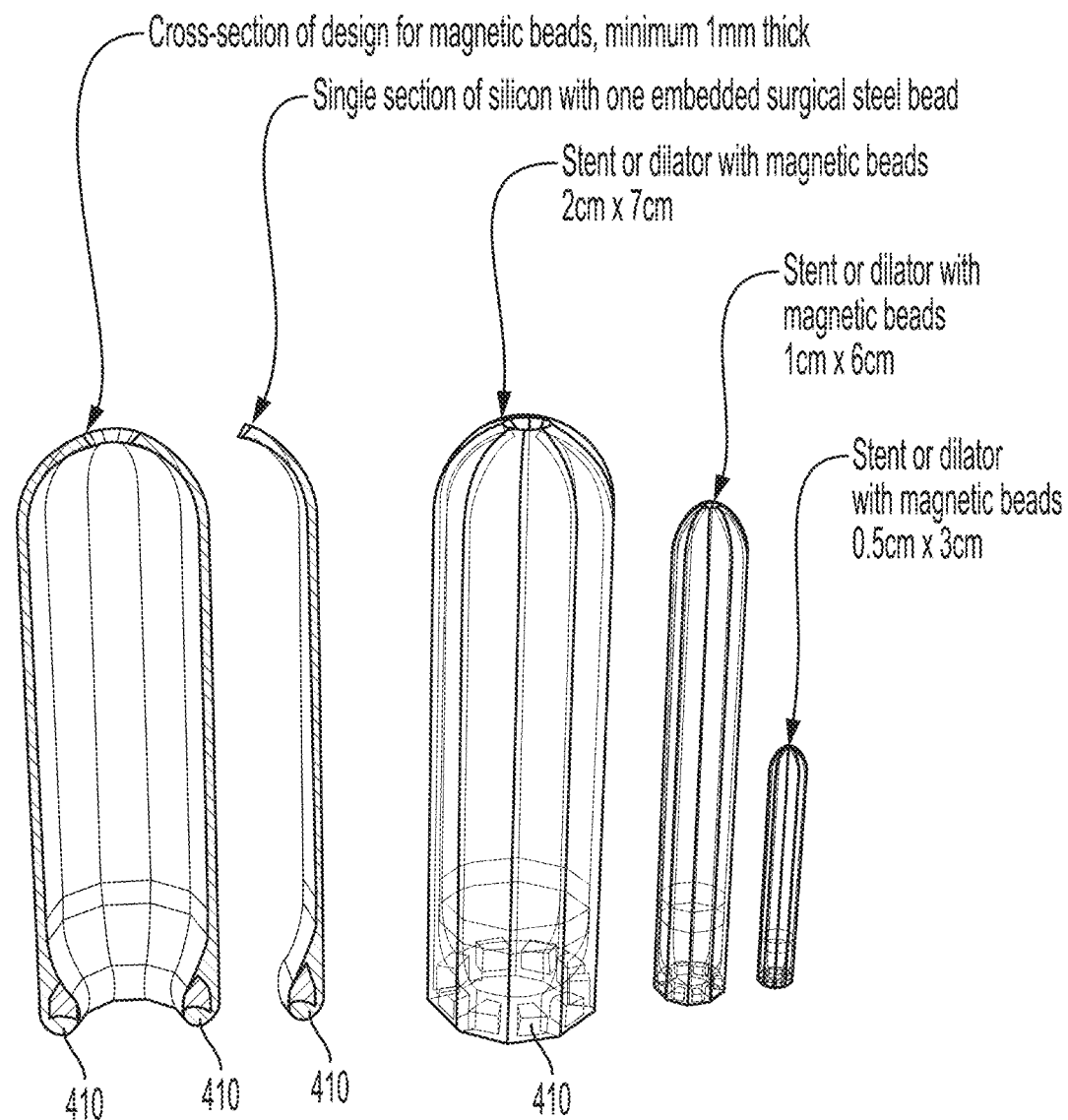
Figure 4C:
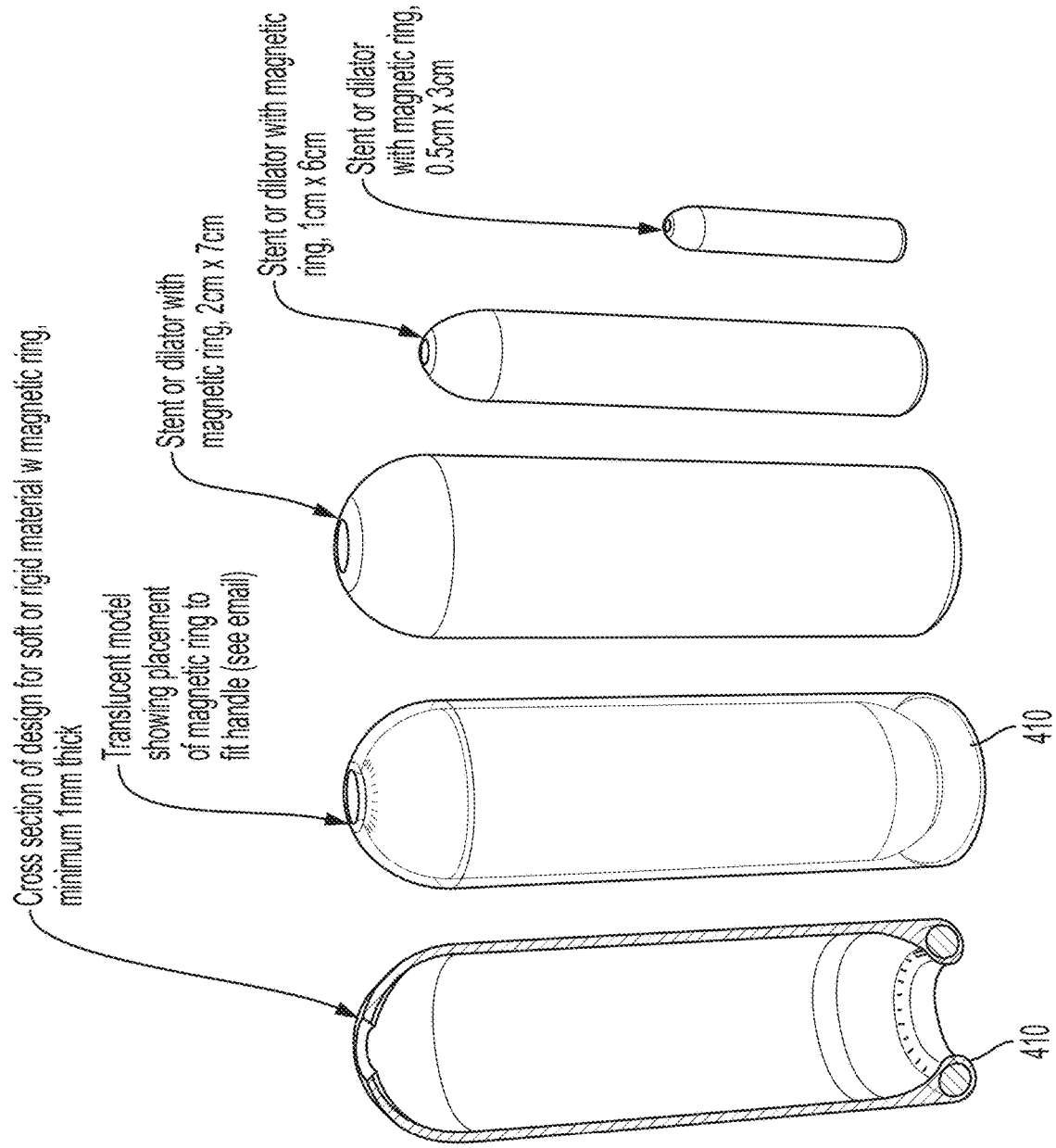
Figure 4D:
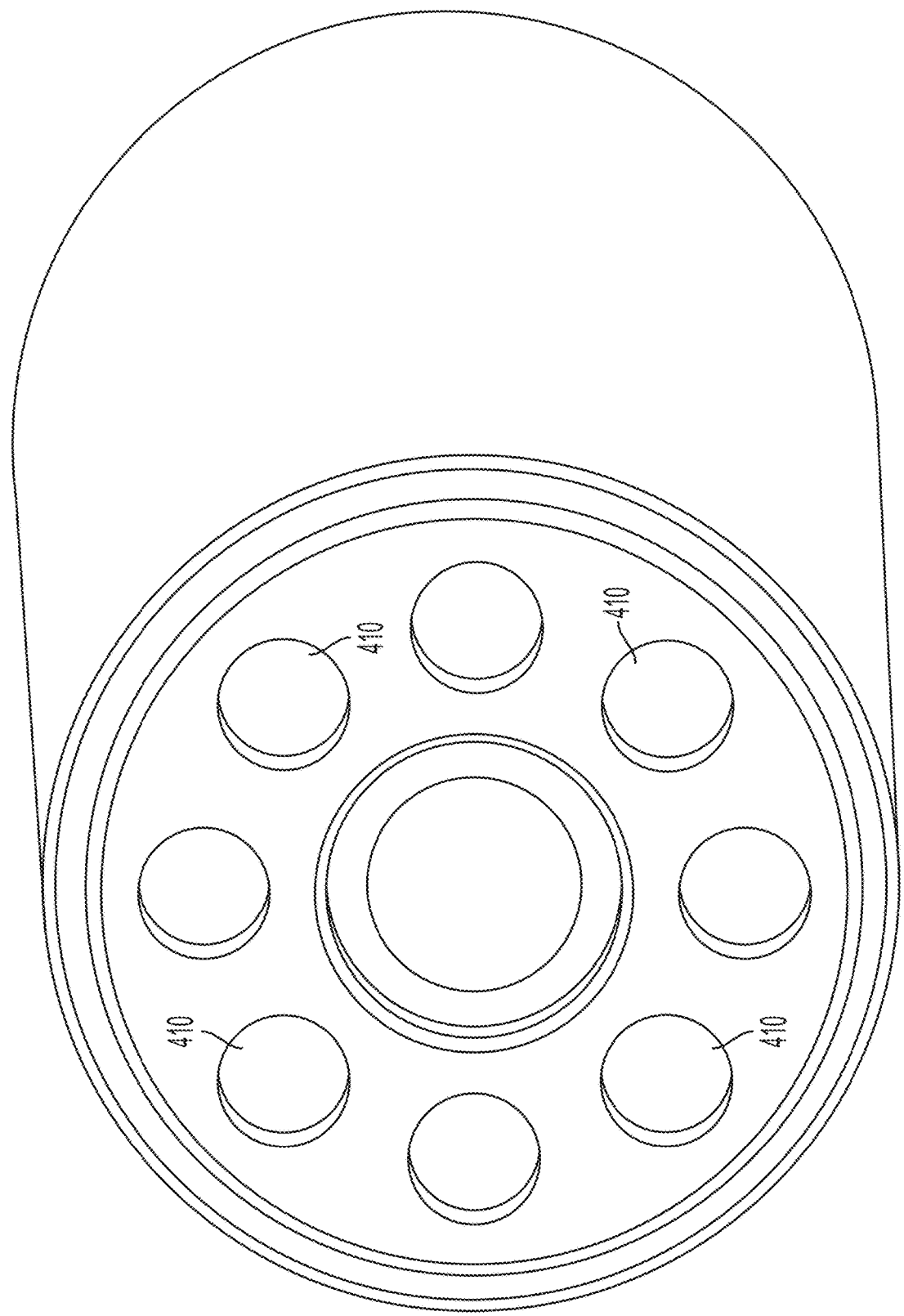

Referring now to FIGS. 4B and 4C, in some embodiments, the vaginal dilator(s) 400 include or are compatible with the use of magnets 410 for engagement with a removable handle 208 for insertion and/or removable. The arrangement of four magnets 410 at 90° radial intervals is depicted in FIG. 4D. In some embodiments, the removable handle 208 is compatible with both the vaginal stents 200 and the vaginal dilators 400.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. An indwelling vaginal stent system comprising:
   an inflatable indwelling vaginal stent comprising:
      a central core adapted and configured to facilitate insertion of the inflatable indwelling vaginal stent prior to inflation, the central core comprising hollow ends and a hollow center to allow for passages of vaginal secretions;
      an elastomeric exterior wall; and
      a first fitting located at a base of the inflatable indwelling vaginal stent; and
   a removable handle adapted and configured for insertion, inflation, and removal of the inflatable indwelling vaginal stent from a subject's vagina, the removable handle including a second fitting complementary to the first fitting and adapted and configured to form substantially fluid tight coupling when the handle is coupled to the inflatable indwelling vaginal stent;
   wherein:
      at least one of the inflatable indwelling vaginal stent and the removable handle comprise one or more magnets of sufficient strength across the subject's perineum to remove the inflatable indwelling vaginal stent from the subject's vagina by placing the removable handle proximate to the subject's perineum; and
      the inflatable indwelling vaginal stent further comprises a magnetically-actuatable valve adapted and configured to deflate the inflatable indwelling vaginal stent when the removable handle is placed in proximity to the base of the inflatable indwelling vaginal stent.

2. The indwelling vaginal stent system of claim 1, wherein the one or more magnets are of sufficient strength to generate between 5 pounds-force and 26 pounds-force across the subject's perineum.

3. An indwelling vaginal stent system comprising:
   an inflatable indwelling vaginal stent comprising:
      a central core adapted and configured to facilitate insertion of the inflatable indwelling vaginal stent prior to inflation, the central core comprising hollow ends and a hollow center to allow for passage of vaginal secretions;
      an elastomeric exterior wall; and
      a first fitting located at a base of the inflatable indwelling vaginal stent; and
   a removable handle adapted and configured for removal of the inflatable vaginal stent from a subject's vagina;
   wherein:
      at least one of the inflatable indwelling vaginal stent and the removable handle comprise one or more magnets of sufficient strength across the subject's perineum to remove the inflatable indwelling vaginal stent from the subject's vagina by placing the removable handle proximate to the subject's perineum; and
      the inflatable indwelling vaginal stent further comprises a magnetically-actuatable valve adapted and configured to deflate the inflatable indwelling vaginal stent when the removable handle is placed in proximity to the base of the inflatable indwelling vaginal stent.

4. The indwelling vaginal stent system of claim 3, wherein the one or more magnets are of sufficient strength to generate between 5 pounds-force and 26 pounds-force across the subject's perineum.

5. The indwelling vaginal stent system of claim 3, wherein:
   the removable handle further comprises a second fitting complementary to the first fitting; and
   when the fittings are engaged, fluid can flow from the removable handle into the inflatable indwelling vaginal stent for inflation.

6. The indwelling vaginal stent system of claim 5, wherein the second fitting is centrally located to the one or more magnets, which are radially arranged.

7. The indwelling vaginal stent system of claim 3, wherein the removable handle includes a pressure gauge to provide feedback regarding the degree of inflation.

8. The indwelling vaginal stent system of claim 3, wherein the central core has a plurality of holes to facilitate flow of fluid into the region bound by the elastomeric exterior wall.

* * * * *

UNITED STATES PATENT AND TRADEMARK OFFICE
CERTIFICATE OF CORRECTION

| | |
|---|---|
| PATENT NO. | : 10,898,699 B2 |
| APPLICATION NO. | : 15/565330 |
| DATED | : January 26, 2021 |
| INVENTOR(S) | : Hakim et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 336 days.

Signed and Sealed this
Tenth Day of January, 2023

Katherine Kelly Vidal
*Director of the United States Patent and Trademark Office*